US005187260A

United States Patent [19]

Karali et al.

[11] Patent Number: 5,187,260

[45] Date of Patent: Feb. 16, 1993

[54] PROCESS FOR THE PREPARATION OF A HIGH PURITY PROTAMINE-DNA COMPLEX AND PROCESS FOR USE OF SAME

[76] Inventors: Sharifa Karali, 143-25 41st Ave., Flushing, N.Y. 11355; John K. Barberii, 4040 E. Kilmer, Tucson, Ariz. 85711

[21] Appl. No.: 685,593

[22] Filed: Apr. 15, 1991

Related U.S. Application Data

[63] Continuation-in-part of Ser. No. 240,528, Sep. 6, 1988, abandoned.

[51] Int. Cl.[5] .................................. C07K 15; C07K 18; C07K 3/28; C07K 3/20

[52] U.S. Cl. .................................... 530/358; 530/422; 530/423; 530/418; 530/417; 530/419; 530/414; 530/415

[58] Field of Search .............. 530/358, 422, 423, 418, 530/419, 417, 414, 415

[56] References Cited

U.S. PATENT DOCUMENTS

| | | | |
|---|---|---|---|
| 4,415,553 | 11/1983 | Zhabilov et al. | 424/95 |
| 5,015,569 | 5/1991 | Pontius | 435/6 |
| 5,053,326 | 12/1991 | Renz | 435/6 |

OTHER PUBLICATIONS

Wienhuer et al. 1987, DNA 6(1):81-89.
Morgan et al. 1983, J. Virol. 46(1):177-186.
Scaner et al. 1956, Tissue Sympathin 63:565-576.

*Primary Examiner*—Robert A. Wax
*Assistant Examiner*—Keith C. Furman
*Attorney, Agent, or Firm*—Michael I. Kroll

[57] ABSTRACT

A process is disclosed in which high purity protamine-DNA complexes are prepared by collecting nucleo-protamines specific developmental stages of a life form, specifically, amphibian, egg by low temperature processing. The process also includes the steps of sequential homogenization in a high concentration aqueous salt solution at a buffered low pH, followed by ultracentrifugation to remove insoluble matter. Either a crude mixture or pure isolate of the complexes may be produced. Pure isolates require aqueous chloroform extraction to isolate protein and to remove lipids. Lyophilization then removes chloroform and excess water. The isolate is then fractionated by single pass alumina chromatography. Dialysis against pure water removes salts. Repeated lyophilization removes excess water and concentrates single protamines and protamine-like proteins. The mixture may then be reconstituted with 5% weight/volume heterologous or homologous DNA, in order to shield from charge toxicity. Crude mixtures may be produced by precipitating the supernate of ultracentrifugation in pure water, followed by ultracentrifugation to sediment in solids. Lyophilization then removes any water from the damp solids. The crude solids are suitable for oral use, especially if utilized in gelatin capsules. Sterile filtration to injection quality aqueous form. Following isolation of the protamine-DNA complex, encapsulation of the prepared solid or aqueous protamine-DNA complexes in a specific carrier substance may be accomplished, depending upon the target tissue for the protamine. Several encapsulation carriers are known from prior art literature, such as, for example, liposomes and nanoparticles. The protamine-DNA complexes of the present invention are useful in inhibiting tumor growth, among other uses.

30 Claims, No Drawings

PROCESS FOR THE PREPARATION OF A HIGH PURITY PROTAMINE-DNA COMPLEX AND PROCESS FOR USE OF SAME

CROSS-REFERENCE TO RELATED APPLICATION

This application is a continuation-in-part of application Ser. No. 07/240,528, filed Sep. 6, 1988, now abandoned.

BACKGROUND OF THE INVENTION

1. Technical Field of the Invention

The present invention relates, generally, to a process for the preparation and use of chemotherapeutic agents.

More particularly, the present invention relates to a process for the preparation of high purity nucleoprotamine-DNA complex substances and a process for their use as an anti-tumor or anti-viral agent, including their use as an anti-AIDS agent. Additionally, research data exists to further suggest that certain aging characteristics, in test animals, might be slowed, or even reversed, with the foregoing chemical agents.

The nucleoprotamine-DNA complex substances are also useful in a variety of other medical conditions, some of which are serious, in humans and other mammals. Elevated serum cholesterol levels have also responded favorably to treatment.

2. Description of the Prior Art

Nucleohistones have been generally known to the art to be closely associated with DNA, and research evidence exists to suggest that such substances protect DNA by wrapping about the double helix of the DNA in adult cells. Hnilica, Lubomir S., *The Structure and Biological Functions of Histones*, p. 37 (CRC Press 1972). By contrast, nucleoprotamines are physically associated with the DNA of embryonic tissue and are not found in adult cells.

Nucleohistones and nucleoprotamines, however, do possess several common characteristics: Both are generally low molecular weight polypeptides (<30,000 Dalton), rich in the amino acid arginine, slowly soluble in water, and resistant to heat coagulation. Both histones and protamines have overall positive charges and are in the basic range of pH. Additionally, both are bound to the negative charge of DNA, with known affinity constants, and both are shielded by the negative charge of DNA. Histones are known to be soluble in very dilute mineral acids, but insoluble in mild aqueous $NH_4OH$. By contrast, protamines are soluble in both very dilute mineral acids and mild aqueous $NH_4OH$.

In the past several years, various research investigators have suggested that histones, and possibly protamines and protamine-like polypeptides, exert a control function over DNA through a direct physical contact, or a lack thereof, at a myriad of sites along the DNA in the genome of all living cells. This direct physical contact at the molecular level constitutes charge cloud interactions between the proteins and the deoxyribose background. The isolation of only a few histone and protamine subunits, and the monotony of their amino acid sequences in different tissues from the same animal, and even from different animals, has suggested that histones and protamines act as merely a protective wrapper for the cellular DNA and lack the expected variability in their amino acid sequence to control transcription of messenger RNA (mRNA).

Furthermore, the structural theories about DNA have suggested that DNA helices have a major and minor groove along the alpha-helix. DNA bases appear to be in the bottom of the major groove, and the deoxyribose backbone in the bottom of the minor groove. Speculation that sequence specific proteins may attach at either the minor or major groove sites, along with histone and protamines or protaminelike proteins, to control transcription or DNA, has been widely accepted. See, Li, Hsueh Jei, *Chromatin and Chromosome Subunits*, Academic Press, New York (1977).

Simple systems for the control of DNA expression are also well known to the prior art, such as the Lactose Operon (LAC Operon) system of prokaryotic cells. An analysis of this operon model illustrates the concept of repressors and inducers as being fundamental control systems for mRNA transcription. See, e.g., Kim, R., and S. H. Kim, "Direct measurement of DNA unwinding angle in specific interaction between lac operator and repressor." *Cold Spring Harbor Symp. Quant. Biol.*, 47: 481–484 (1983); Wang, J., M. D. Barkley, and S. Bourgeois, "Measurements of unwinding of lac operator by repressor." *Nature*, 251: 247–249 (1974).

In the LAC Operon, a promoter site on the DNA is followed by an operator site and structural gene sequences for three enzymes required for the hydrolysis and control of the galactose to glucose metabolic pathway. Galactose, along with catabolite activator protein (CAP), cyclic AMP (c-AMP), and RNA polymerase are capable of acting as an inducer, displacing the LAC repressor protein from the operator site, presumably accessable through the major groove, binding with the promoter site, and allowing transcription of the structural genes to proceed. If glucose is present, it acts to block the formation of the active inducer complex and the cell's own heterogeneous repressor remains attached to the operator site, with no transcription of the LAC genes possible.

Thus, by negative feedback inhibition, glucose controls the transcription of the LAC operon. Repressors, under this theory, have a negative influence on transcription, and this is an important aspect of control which the invention focuses upon.

By way of background, repressors may have developed, through evolution, as mutations, or acquired oncogenes, in very early unicellular promordial organisms. A mutant, with an incomplete repressor, may have had a competitive, if not at least a metabolic advantage, if it could halt the production of a protein when the protein was sufficiently abundant in the cytoplasm, and then re-start production of the protein as the need was developed in the cell. It is postulated that a mutant with an incomplete repressor would consume less energy than those of a normal phenotype and would be favored for survival under the theory of natural selection. Complete repressor mutants must have obviously died, if the synthesis of the particular protein so repressed was critical for survival. However, the incomplete repressor mutant could have survived if the repressor was only "loosely" attached to the operator site, and a cellular protein, or lack of such protein, influenced the repressor to "fall off" the particular operator site.

Now consider obligate parasites, such as a virus. For such parasites to have the ability to shut-down a host cell's transcription of proteins for the host cell, so that the "pirated" cellular machinery could be utilized to transcribe viral proteins, would yield such "life" forms a tremendous evolutionary advantage. Again, by evolution and mutation, viruses may have developed their own cell-directed repressors, encoded into viral DNA or RNA, transcribed when the virus DNA infected the host DNA, or translated from viral RNA, and subsequently pre-packaged with the viral genetic material during lysogeny phase in prokaryotic cells. Evidence that transcription of prokaryotic cellular proteins frequently ceases within minutes after viral infection, strongly supports this theory. Stryer, Lubert, *Biochemistry*, p. 712 (W. H. Freeman and Company, San Francisco, 1975.)

The infection of eukaryotic cells, by contrast, rarely leads to a total shutdown of host transcription, but rather, results in subtle repressor mediated subversion of both cytoplasmic and nuclear host process; possibly the next stage in the evolutionary process, avoiding a less energy efficient total shutdown.

Consider the specificity of the foregoing types of repressors, one of homogenetic cellular origin, and one, what is recognized by the cell to be, of allogenetic viral origin. The cell's repressor (C-rep) has evolved a very specific operator region to match its complementary operator site (e.g., only 27 base-pairs long, with some symmetry, in *E. coli.*), with matched base sequence by base pair to base pair in the operator region; a form of evolved primary structure, with a high rate constant of association (e.g., $7\times10^{9}$ m$^{-1}$ in *E. coli.*); and, other primary, secondary, tertiary and quarternary protein structural evolutions in the remainder of the specialized globular protein (approximately 30,000 Daltons) to interpret the various cytoplasmic signals that dictate to "release" or "remain attached." Stryer, Lubert, *Biochemistry, p.* 684 (W. H. Freeman and Company, San Francisco, 1975.)

Concerning the viral repressor (V-rep), originating from a viral DNA (or, in some cases, RNA) strand of small proportions (e.g., $10^{6}$–$10^{7}$ Daltons) (Stryer, Lubert, *Biochemistry*, p. 709 (W. H. Freeman and Company, San Francisco, 1975.)), it would be of great advantage to the viral repressor if it were to successfully complement the base pairing of the operator region in a number of host cells. This would be expected if the base pairing in the operon anticodon region of the V-rep was less specific than that of the C-rep. In short, viruses, and possibly other living organisms, have probably evolved poor fitting, but nonetheless effective repressors, when at an evolutionary advantage to do so. In fact, as discussed above, perfectly fitting repressors could conceivably act as complete repressors, thereby possibly having a lethal effect on the cell.

Consider, now, the situation presented when a host cell is under attack or otherwise infected by an assortment of viral agents and other life forms; poorly fitting allogenetic repressors, repressors evolved without the globular protein structure necessary for their timely removal at specific intracellular prompt conditions. Under such conditions, it is clear that the control of protein synthesis within the cell may be severely affected.

Now, reconsider the postulated evolutionary trends of repressors, but now allow for inducers, globlar proteins (or combinations of proteins) that greatly enhance m-RNA transcription rates, to also be imitated. Not only are host cells producing less of some proteins due to repression, but the host may actually begin to produce greater amounts of other proteins due to allogenetic inducers. False allogenetic repression and induction may completely disrupt a cell's metabolic process, and at the simplest level, the disruption of a cell's normal metabolic processes are the classic causes of cancer.

The general histological changes of tissue associated with the regression of a cell toward a cancer are known. Such cells are less differentiated, tend to function and appear as embryonic tissues and have been described as chaotic in their metabolic pathways and metastatic without regard to their proper location.

Thus, control of protein synthesis means proper health for a cell. Conversely, the lack of control or proper regulation of protein synthesis results in aberrant metabolism, dysfunction and sometimes even death of the cell.

The theory behind nucleoprotamine therapy states that the treatment of mammals with specifically timed collections of extracted nucleoprotamine and protamine-like proteins removes false repressors and false inducers, due to the lack of complete operon affinity in these heterogenetic proteins.

Additionally, consider an important adult tissue operon (a length of genetic coding sequence required to make a protein necessary for the health of the cell) that has been repressed by a repressor protein of allogentic origin, such a viral protein from a recent viral infection. Adaptation of Wilkin's 1956 model depicts an allogenetic repressor occupying the major groove of the DNA helix over an operator region. Wilkins, M. H. F., *Physical Studies of the Molecular Structure of Deoxyribose Nucleic Acid and Nucleoprotein*, Cold Spring Harbor Symposium Quantitative Biology, 21, 75–90 (1956). The allogenetic repressor is, in all likelihood, poorly physically bound to the operator region of the operon thereby physically preventing the attachment of the RNA polymerase to make the mRNA template of the protein. There is a physical relationship in a three-dimensional linear arrangement between the DNA of the operon, the normal closely applied histone molecules (generally less than 10,000 Daltons MW) about the DNA double helix, and the allogenetic repressor protein, typically 19,000 to 40,000 Daltons MW, sitting astride the DNA operator site, with its molecular structure displacing the histone from the area of the minor groove. From Rauka's model in 1966, and in agreement with Inoue and Ando's 1969 model of nucleoprotamine structure, the protamine, like histone, may occupy the minor groove of the DNA double helix, but also affect the binding sites of the major groove of Wilkin's 1956 model by charge cloud or physical interaction. Ando, T., Yamasaki, M., Suzuki, K., *Protamines, Isolation, Characterization, Structure and Function.* Molecular Biology, Biochemistry and Biophysics, V. 12, p. 81–84 (1973); and, Li, Hsueh Jei, *Chromatin and Chromosome Subunits*, pp. 159–161 (Academic Press, New York, 1977).

There is no excess histone in the free state in cells, due to highly toxic effects from the positive charge. Protamine, like histone, is a structural protein, but evolutionarily a protein of embryonic origin with nearly twice ($K_B=15.0M^{-1}$) the DNA binding coefficient of histone IV ($K_B=7.5M^{-1}$) at near physiological saline (0.154M aqueous NaCl). See, Table 1.

TABLE 1

Binding of Basic Proteins to DNA[1], Values of Binding Coefficient[2], $K_B$ ($M^{-1}$), in 0.1 M and 0.95 M NaCl

| | Binding Coefficients (× $10^2$) | | | |
|---|---|---|---|---|
| | In 0.1 M NaCl Maximum Binding | | In 0.95 NaCl Minimum Binding | |
| Protein | Native DNA | Denatured DNA | Native DNA | Denatured DNA |
| Protamine | 15.0 | 5.9 | 1.2 | 0.6 |
| Histone IV | 7.5 | 5.1 | 1.8 | 1.3 |
| Histone Ib | 1.9 | 1.8 | 0.4 | 0.6 |
| Poly-L-lysine | 2.1 | 1.9 | 1.6 | 1.2 |

[1]Akinrimisi, E. D., J. Molecular Biology, "Binding of Basic Proteins to DNA", 11, 128–136 (1965).

$$^{2}\text{Binding Coefficient } (K_B[M^{-1}]) = \frac{\text{Moles of Protein Amino Nitrogen Bound}}{(\text{DNA Concentration in moles nucleotide per liter}) \cdot (\text{Moles of Protein Amino Nitrogen Free})}$$

Protamine represents an early, evolutionary solution to the onslaught of allogenetic false inducers and false repressors.

After administered protamine-DNA complexes arrive in the repressed cell, there is a relative abundance of protamine, as compared with functional cellular DNA. Watters, C., Gullino, P., "Translocation of DNA from the Vascular into the Nuclear Compartment of Solid Mummary Tumors," *Cancer Research* 31, 1231–1243 (September 1971). The DNA in the adult cells is only protected by histones. The affinity of protamine for the DNA is, evolutionarily, greater than that of histone. The protamine dissociates from the allogenetic DNA and attaches to the open minor groove, due to its high binding affinity, replacing the lost histone and weakening the attachment of the allogenetic repressor. The allogenetic repressor is then displaced. DNAases in the cytoplasm attack the exposed allogenetic DNA, left instantaneously vacant by a protamine molecule in equilibrium, with the cell's DNA at the minor groove. The expelled allogenetic repressor is destroyed by circulating protease, or at least diffuses away from the major groove. Finally, the protamine is randomly, and slowly, replicated by histones. The cell's own repressors may now control the operator region, and transcription of DNA again. The cell returns to a normal genetic when a sufficient amount of allogenetic repressors are displaced to stop further uncontrolled transcription of unwanted proteins.

Displacement of allogenetic repressor by protamine interaction on the minor groove leads to normal translation of major groove base pairs.

The actual substitution of protamine follows a simple competitive inhibition model where the success of replacing the foreign repressor protein is directly proportional to a high protamine-DNA/foreign repressor ratio. The reaction is also influenced by the destruction of the allogenetic DNA of the original protamine-DNA complex, stopping the return of the protamine molecule to the allogenetic donor from the cell's heterogenetic DNA, thus, making the reaction irreversible.

SUMMARY OF THE INVENTION

It is, therefore, an object of the present invention to provide an improved process for the production of high purity nucleoprotamine-DNA complex substances.

It is yet a further object of the invention to provide a process for the use of nucleoprotamine-DNA complex compounds as anti-tumor or anti-viral agents.

The foregoing and related objects are accomplished by a process in which high purity protamine-DNA complexes are prepared by collecting nucleoprotamines specific developmental stages of a life form, specifically, fertilized amphibian, egg by low temperature processing. The process also includes the steps of sequential homogenization in a high concentration aqueous salt solution and a citric acid buffer, at a low pH of approximately 2.2, followed by ultracentrifugation to remove insoluble matter. These steps are then followed by an aqueous chloroform extraction to isolate protein and to remove lipids and lyophilization. Single pass alumina chromatography is then used to separate each active protamine and protamine-like basic fraction. Dialysis against pure water removes excess salt, and lyophilization increases concentration of each separated protamine and protamine-like protein. Each isolate may then be reconstituted with 5% weight-volume heterologous or homologous DNA, in order to shield from charge toxicity. Sterile filtration produces injection quality physiologic aqueous form. Optionally, a precipitation in sterile pure water, followed by lyophilization to remove water and to produce a solid form of the protamine-DNA complex obtained, is also recommended for dry preservation.

Following isolation of the protamine-DNA complex, encapsulation of the prepared solid or aqueous protamine-DNA complexes, in a specific carrier substance, may be accomplished, depending upon the target tissue for the protamine. Several encapsulation carriers are known from prior art literature, such as, for example, liposomes and nanoparticles.

DETAILED DESCRIPTION OF THE PREFERRED EMBODIMENTS

Turning now, in detail, to a consideration of the preferred embodiments of the present invention, each developmentally-timed nucleoprotamine has a utility for inhibiting tumor cell growth; inhibiting viral reproduction; and, regulating mammalian cellular metabolism by directly influencing DNA transcription at the macromolecular level—a phenomenon that may delay, or even reverse, the observed physiological changes we associate or attribute to aging.

More particularly, the present invention concerns a process that allows for the maximum extraction of nucleoprotamine from any fertilized egg source with the protamine being extracted at the proper time during embryonic development.

In research thus far conducted, fertilized amphibian eggs from the common grass frog *Rana pipiens*, were used. In the following example of the invention, all steps were carried out with an aseptic technique at 4° C., unless otherwise noted.

At a proper time, known to those skilled in the art, artificailly inseminated live incubating eggs were harvested whole from oxygenated 67° F.-shallow laminar flow, 5% weight/volume DeBoer's bath and are identified in the proper stage of development. Eggs in early to mid-gastrula states, as depicted by Witschi stages 8 and 9 (Witschi, Emil, *Development of the Vertibrates*, W. B. Saunders Company, New York 1956) have been quite satisfactory, however, other stages may be equally suitable. The eggs are then snap frozen with liquid nitrogen to halt development, and placed at −40° C. for long-term storage.

Anytime thereafter, though preferably within a few weeks, the eggs may be defrosted at room temperature and mixed with an equal volume of 4M aqueous NaCl solution buffered to pH 2.2 with 1/10 volume 0.1M sodium citrate.

Tissue homogenation was accomplished with a Brinkman Polytron homogenizer set on #6, as understood in the art, for 4 to 5 minutes until all the eggs are finely ground into a thick gray emulsion. This thick emulsion is ultra-centrifuged at 15,000+ g's for 15 minutes in a refrigerated centrifuge. The cloudy, gray supernate is then easily poured off the brown and black granular sediment. This supernate contains the cytoplasm, without organelles, and nucleoplasm, with unbound nucleoprotamine released from its close relationship with DNA by the high concentration of salt and acidic pH. Serum protein electrophoresis, at this stage, further shows a crude, but relatively pure Beta electrophoretic range protein peak, i.e., the crude, protamine-DNA (CPDNA).

Further processing includes chloroform extraction of protein. This requires the addition of 0.1 g of $Na_2CO_3$ per 20 cc of supernate, stirred incubation at 50° C. for 30 minutes at an adjusted pH of 7 with glacial acetic acid, and the addition of an equal volume of chloroform with 0.1 volume amyl alcohol. The mixture is then shaken for 10 minutes and centrifuged to separation at 2,000 g. The topmost pure aqueous layer of the resultant three-layer liquid is discarded. The middle layer, being of chloroform-alcohol-protein is removed from the lower layer of chloroform waste, and saved. This middle layer is then lypholized at 0.001 torr and −40° C. to remove the volatile chloroform. The fluffy precipitate is the purified protamines, identified by basic Isoelectric Focusing (IEF), with a pI of approximately 9.50. Further purification involves separating the purified protamines and protamine-like proteins into discrete fractions by alumina chromatography. The column was loaded with 0.4 cc of 2 mg/cc purified protamine mixture, and developed with 0.45M aqueous $K_2HPO_4$ at a flow rate of 0.25 cc/min. Pierce Chemical Company BCA Protein Reagent was used to identify the protein concentration at 562 nm visible light spectrum on a DU-7 spectrophotometer. Albumin protein standards were used for calibration. Each fraction of protamine may be precipitated with DNA upon dialysis against pure water.

Due to the strong positive charge of the protamine base, a minimum of 5 mol % of DNA must be added back to the mixture to cover the strong positive charge of the free base, which is quite toxic, in and of itself, to test animals.

The salt content in the foregoing procedure, can be reduced to 0.09% (physiologic) saline by dialysis against pure water. Addition of DNA at approximately 5.0 mol percent causes microprecipitation during dialysis. This results in reconstitution of protamine-DNA via microprecipitation of the free base protamine with the available 1:1 mole ratio DNA and reduced toxicity. Final bacteriologic microfiltration with 0.22 micron USP stainless approved equipment is necessary for human injection quality extract, which is also suitable for various forms of encapsulation.

The DNA used in reconstitution may be of heterogenetic or homogenetic origin, i.e., from the protamine donor tissue or the target tissue. This reconstituted protamine-DNA complex (RPDNA) can then be encapsulated and directed more specifically to target tissues.

The crude protamine-DNA (CPDNA) may be precipitated to form wispy white tendrils in sterile double distilled water. This precipitate is easily separated by repeated centrifugation at 15,000 g's and decanting off the supernate. The wet precipitate can be crystalized in a lypholizer at 0.001 torr and −40° C. until reduced to an amorphous light brown sticky material, with the consistency of coarse cotton candy.

This solid is readily weighed and packed in gelatin capsules for oral use, as the low molecular weight protamine-DNA complex is readily absorbed across the mammalian gut in non-specific administration protocols. The properties of this solid phase are essentially the same as the purified material, except for the higher percentage of donor tissue DNA.

The invention will now be further described by means of an additional testing procedure and data. It should, of course, be recognized that the following is merely illustrative of the invention and is not intended to define the limits thereof.

In the following testing protocol, testing data is presented as tumor size, calculated volume and growth curves during in vivo testing against B16F10 murine melanoma in C57BL6 mice, modeled after the National Cancer Center Protocols, for limited cohort group testing.

In this protocol, 20–25-gram four-week old C57BL6 mice were implanted with $1\times10^6$ B16F10 murine melanoma, pass 35, tumor cells from cell culture stocks, by injection into the muscle mass of the right thigh on Day 0. Treatment was begun on Day 1, by intraperitoneal injection of CPDNA daily, except on noted days when treatment was withheld due to dose related toxicity. Additionally, intratumor injections of CPDNA were administered, adjunctively, on noted days.

Controls received only similar intratumor injections with normal saline on like days and no intraperitoneal injections. Tumors were measured with calipers on a daily basis and volumes were calculated for an average radius from two dimensional diameter measurements according to the following formula:

$$V=[(d_1+d_2)/4]^2 \quad \text{pI}$$

The volume of a given mouse's leg on Day 0 was subtracted from the calculated total volume of the tumor to give the net tumor volume (NTV). (See, Tables 2, 3 and 4.)

As noted from the results presented in the accompanying Tables, the test group, as opposed to the control group, generally had a smaller amount of net tumor volume. (See, Table 4.)

While only several embodiments of the present invention have been shown and described, it will be obvious to those of ordinary skill in the art that many modifications may be made to the present invention without departing from the spirit and scope thereof.

TUMOR DATA SIZE (in mm³)

| Date | | Control Group | | | | | Test Group | | | | | Dose & |
|---|---|---|---|---|---|---|---|---|---|---|---|---|
| Mouse # | Day | 1 | 2 | 3 | 4 | 5 | 1 | 2 | 3 | 4 | 5 | Route |
| 12/29/87 | 0 | All mice receive 1 × 10⁶ cells B16F10 melanoma IP | | | | | | | | | | |

-continued

TUMOR DATA SIZE (in mm$^3$)

| Date Mouse # | Day | Control Group 1 | Control Group 2 | Control Group 3 | Control Group 4 | Control Group 5 | Test Group 1 | Test Group 2 | Test Group 3 | Test Group 4 | Test Group 5 | Dose & Route |
|---|---|---|---|---|---|---|---|---|---|---|---|---|
| 12/30/87 | 1 | 6 × 5 | 5 × 5 | 5 × 5 | 5 × 5 | 5 × 5 | 5 × 5 | 5 × 5 | 5 × 5 | 5 × 5 | 5 × 5 | 0.1 cc IP |
| 12/31/87 | 2 | 6 × 5 | 5 × 5 | 5 × 5 | 5 × 5 | 5 × 5 | 5 × 5 | 5 × 5 | 5 × 5 | 5 × 5 | 5 × 5 | |
| 1/1/88 | 3 | 6 × 5 | 5 × 5 | 5 × 5 | 5 × 5 | 5 × 5 | 5 × 5 | 5 × 5 | 5 × 5 | 5 × 5 | 5 × 5 | 0.1 cc IP |
| 1/2/88 | 4 | 6 × 5 | 5 × 5 | 5 × 5 | 5 × 5 | 5 × 5 | 5 × 5 | 5 × 5 | 5 × 5 | 5 × 5 | 5 × 5 | |
| 1/3/88 | 5 | 6 × 5 | 5 × 5 | 5 × 5 | 5 × 5 | 5 × 5 | 5 × 5 | 5 × 5 | 5 × 5 | 5 × 5 | 5 × 5 | |
| 1/4/88 | 6 | 6 × 5 | 5 × 5 | 5 × 5 | 6 × 5 | 6 × 5 | 5 × 5 | 5 × 5 | 5 × 5 | 5 × 5 | 5 × 5 | |
| 1/5/88 | 7 | 6 × 5 | 5 × 5 | 5 × 5 | 6 × 5 | 6 × 5 | 5 × 5 | 5 × 5 | 5 × 5 | 5 × 5 | 5 × 5 | |
| 1/6/88 | 8 | 6 × 5 | 6 × 5 | 5 × 5 | 7 × 5 | 6 × 5 | 5 × 5 | 5 × 5 | 6 × 5 | 6 × 5 | 6 × 5 | 0.4 cc IP |
| 1/7/88 | 9 | 7 × 5 | 7 × 5 | 5 × 5 | 7 × 7 | 6 × 5 | 5 × 5 | 5 × 5 | 6 × 5 | 6 × 5 | 6 × 5 | 0.4 cc IP |
| | | | | | | | | | | | | 0.1 cc IT |
| 1/8/88 | 10 | 8 × 7 | 7 × 7 | 7 × 6 | 8 × 7 | 7 × 7 | 7 × 5 | 6 × 5 | 7 × 7 | 7 × 7 | 7 × 5 | 0.6 cc IP |
| | | | | | | | | | | | | 0.1 cc IT |
| 1/9/88 | 11 | 10 × 10 | 12 × 10 | 7 × 7 | 13 × 13 | 10 × 10 | 8 × 7 | 8 × 7 | 10 × 8 | 9 × 8 | 8 × 7 | 0.5 cc IP |
| | | | | | | | | | | | | 0.3 cc IT |
| 1/10/88 | 12 | 12 × 11 | 13 × 12 | 8 × 7 | 15 × 14 | 13 × 11 | 8 × 7 | 9 × 8 | 10 × 8 | 10 × 10 | 9 × 8 | 0.5 cc IP |
| | | | | 3 × 3* | | | | | | | | 0.3 cc IT |
| 1/11/88 | 13 | 14 × 14 | 14 × 14 | 9 × 6 | 16 × 15 | 14 × 15 | 9 × 8 | 7 × 8 | 11 × 10 | 11 × 10 | 10 × 9 | 0.6 cc IP |
| | | | | 7 × 7* | | | | | | | | 0.4 cc IT |
| 1/12/88 | 14 | 14 × 14 | 14 × 14 | 10 × 10 | 17 × 17 | 15 × 16 | 10 × 9 | 9 × 8 | 11 × 10 | 10 × 10 | 10 × 8 | No Rx |
| | | | | 8 × 8* | | | | | | | | |
| 1/13/88 | 15 | 16 × 15 | 16 × 16 | 10 × 10 | -D- | 17 × 17 | 10 × 10 | 9 × 9 | 12 × 12 | 13 × 11 | -D- | 0.5 cc IP |
| | | | | 10 × 10* | | | | | | | | |
| 1/14/88 | 16 | 18 × 19 | 18 × 18 | 13 × 13 | -D- | 17 × 20 | 10 × 10 | 10 × 9 | 14 × 12 | 14 × 13 | -D- | 0.5 cc IP |
| | | | | 10 × 10* | | | | **D** | | | | 0.3 cc IT |
| 1/15/88 | 17 | 19 × 20 | 20 × 20 | 14 × 20 | -D- | 17 × 20 | 10 × 10 | -D- | -D- | 16 × 14 | -D- | No Rx |
| 1/16/88 | 18 | 21 × 21 | 22 × 22 | 15 × 22 | -D- | -D- | 11 × 10 | -D- | -D- | 18 × 16 | -D- | 0.5 cc IP |
| 1/17/88 | 19 | 22 × 22 | 23 × 22 | 18 × 24 | -D- | -D- | 13 × 13 | -D- | -D- | 19 × 17 | -D- | No Rx |
| 1/18/88 | 20 | 24 × 24 | 23 × 23 | 21 × 26 | -D- | -D- | 14 × 15 | -D- | -D- | 20 × 18 | -D- | 0.5 cc IP |
| 1/19/88 | 21 | 26 × 26 | 24 × 26 | 21 × 27 | -D- | -D- | 16 × 19 | -D- | -D- | 21 × 20 | -D- | 0.4 cc IP |
| 1/20/88 | 22 | 27 × 27 | 26 × 26 | 23 × 29 | -D- | -D- | 14 × 15 | -D- | -D- | 22 × 20 | -D- | No Rx |
| 1/21/88 | 23 | 27 × 28 | -D- | 24 × 29 | -D- | -D- | 21 × 22 | -D- | -D- | 22 × 20 | -D- | No Rx |
| 1/22/88 | 24 | 28 × 29 | -D- | 26 × 30 | -D- | -D- | 22 × 24 | -D- | -D- | 24 × 29 | -D- | No Rx |
| 1/23/88 | 25 | -D- | -D- | -D- | -D- | -D- | 23 × 24 | -D- | -D- | -D- | -D- | No Rx |
| 1/24/88 | 26 | -D- | -D- | -D- | -D- | -D- | 24 × 26 | -D- | -D- | -D- | -D- | No Rx |
| 1/25/88 | 27 | -D- | -D- | -D- | -D- | -D- | -D- | -D- | -D- | -D- | -D- | No Rx |

KEY TO TABLE
IP indicates intraperitoneal injection route.
IT indicates intratumor injection route.
*indicates a satellite mass arising next to implant site.
D indicates animal died in seconds due to accidental intrarterial injection.
-D- indicates animal found dead in cage.

NET TUMOR VOLUME DATA (all volumes in mm$^3$)

| Date Mouse # | Day | Control Group 1 | Control Group 2 | Control Group 3 | Control Group 4 | Control Group 5 | Test Group 1 | Test Group 2 | Test Group 3 | Test Group 4 | Test Group 5 |
|---|---|---|---|---|---|---|---|---|---|---|---|
| 12/29/87 | 0 | All mice receive 1 × 10$^6$ cells B16F10 melanoma IP; Control volumes calculated for normal leg size: | | | | | | | | | |
| 12/30/87 | 1 | 23.8 | 19.6 | 19.6 | 19.6 | 19.6 | 19.6 | 19.6 | 19.6 | 19.6 | 19.6 |
| 12/31/87 | 2 | 0 | 0 | 0 | 0 | 0 | 0 | 0 | 0 | 0 | 0 |
| 1/1/88 | 3 | 0 | 0 | 0 | 0 | 0 | 0 | 0 | 0 | 0 | 0 |
| 1/2/88 | 4 | 0 | 0 | 0 | 0 | 0 | 0 | 0 | 0 | 0 | 0 |
| 1/3/88 | 5 | 0 | 0 | 0 | 0 | 0 | 0 | 0 | 0 | 0 | 0 |
| 1/4/88 | 6 | 0 | 0 | 0 | 4.2 | 4.2 | 0 | 0 | 0 | 0 | 0 |
| 1/5/88 | 7 | 0 | 0 | 0 | 4.2 | 4.2 | 0 | 0 | 0 | 0 | 0 |
| 1/6/88 | 8 | 0 | 4.2 | 0 | 8.7 | 4.2 | 0 | 0 | 4.2 | 4.2 | 4.2 |
| 1/7/88 | 9 | 4.5 | 8.7 | 0 | 18.9 | 4.2 | 0 | 0 | 4.2 | 4.2 | 4.2 |
| 1/8/88 | 10 | 20.4 | 18.9 | 13.6 | 24.6 | 18.9 | 8.7 | 4.2 | 18.9 | 18.9 | 8.7 |
| 1/9/88 | 11 | 54.7 | 75.4 | 18.9 | 113.1 | 58.9 | 24.6 | 24.6 | 44.0 | 37.1 | 24.6 |
| 1/10/88 | 12 | 80.1 | 103.1 | 24.6 | 123.5 | 93.5 | 24.6 | 37.1 | 44.0 | 58.9 | 37.1 |
| | | | | +7.1 | | | | | | | |
| 1/11/88 | 13 | 130.1 | 134.3 | 24.6 | 169.1 | 145.5 | 37.1 | 24.6 | 67.0 | 67.0 | 51.3 |
| | | | | +38.5 | | | | | | | |
| 1/12/88 | 14 | 130.1 | 134.3 | 58.9 | 207.4 | 169.1 | 51.3 | 37.1 | 67.0 | 58.9 | 44.0 |
| | | | | +50.3 | | | | | | | |
| 1/13/88 | 15 | 164.9 | 181.5 | 58.90 | -D- | 207.4 | 58.9 | 44.0 | 93.5 | 93.5 | -D- |
| | | | | +78.5 | | | | | | | |
| 1/14/88 | 16 | 245.0 | 234.9 | 113.1 | -D- | 249.2 | 58.9 | 51.3 | 113.1 | 123.53 | -D- |
| | | | | +78.5 | | | | | | | |
| 1/15/88 | 17 | 274.8 | 294.6 | 207.4 | -D- | 249.2 | 58.9 | -D- | -D- | 157.1 | -D- |
| 1/16/88 | 18 | 322.6 | 360.5 | 249.2 | -D- | -D- | 67.0 | -D- | -D- | 207.4 | -D- |
| 1/17/88 | 19 | 356.3 | 378.0 | 326.8 | -D- | -D- | 113.1 | -D- | -D- | 234.9 | -D- |
| 1/18/88 | 20 | 428.6 | 395.9 | 414.1 | -D- | -D- | 145.5 | -D- | -D- | 263.9 | -D- |
| 1/19/88 | 21 | 507.1 | 471.3 | 432.8 | -D- | -D- | 220.9 | -D- | -D- | 310.5 | -D- |

-continued

NET TUMOR VOLUME DATA (all volumes in $mm^3$)

| Date Mouse # | Day | Control Group 1 | 2 | 3 | 4 | 5 | Test Group 1 | 2 | 3 | 4 | 5 |
|---|---|---|---|---|---|---|---|---|---|---|---|
| 1/20/88 | 22 | 548.8 | 511.3 | 511.3 | -D- | -D- | 294.6 | -D- | -D- | 326.8 | -D- |
| 1/21/88 | 23 | 570.2 | -D- | 531.9 | -D- | -D- | 343.5 | -D- | -D- | 326.8 | -D- |
| 1/22/88 | 24 | 614.1 | -D- | 596.2 | -D- | -D- | 395.9 | -D- | -D- | 531.9 | -D- |
| 1/23/88 | 25 | -D- | -D- | -D- | -D- | -D- | 414.1 | -D- | -D- | -D- | -D- |
| 1/24/88 | 26 | -D- | -D- | -D- | -D- | -D- | 471.3 | -D- | -D- | -D- | -D- |
| 1/25/88 | 27 | -D- | -D- | -D- | -D- | -D- | -D- | -D- | -D- | -D- | -D- |

KEY TO TABLE
+ indicates a satellite tumor that is later engulfed during tumor expansion.
-D- indicates animal found dead in cage.

TABLE 4

AVERAGE NET TUMOR VOLUME (in $mm^3$)

| Date | Day | Controls | Test Group |
|---|---|---|---|
| 12/29/87 | 0 | 0 | 0 |
| 12/30/87 | 1 | 0 | 0 |
| 12/31/87 | 2 | 0 | 0 |
| 1/1/88 | 3 | 0 | 0 |
| 1/2/88 | 4 | 0 | 0 |
| 1/3/88 | 5 | 0 | 0 |
| 1/4/88 | 6 | 4.2 | 0 |
| 1/5/88 | 7 | 4.2 | 0 |
| 1/6/88 | 8 | 5.7 | 4.2 |
| 1/7/88 | 9 | 9.1 | 4.2 |
| 1/8/88 | 10 | 19.3 | 11.9 |
| 1/9/88 | 11 | 64.2 | 31.0 |
| 1/10/88 | 12 | 86.4 | 40.3 |
| 1/11/88 | 13 | 128.4 | 49.4 |
| 1/12/88 | 14 | 150.0 | 51.7 |
| 1/13/88 | 15 | 172.8 | 72.5 |
| 1/14/88 | 16 | 230.2 | 86.7 |
| 1/15/88 | 17 | 256.5 | 108.0 |
| 1/16/88 | 18 | 310.8 | 137.2 |
| 1/17/88 | 19 | 353.7 | 174.0 |
| 1/18/88 | 20 | 412.9 | 204.7 |
| 1/19/88 | 21 | 470.4 | 265.7 |
| 1/20/88 | 22 | 523.8 | 310.7 |
| 1/21/88 | 23 | 551.0 | 335.2 |
| 1/22/88 | 24 | 605.2 | 463.9 |

What is claimed is:

1. A process for providing a high-purity protamine-DNA complex, consisting essentially of the sequential steps of:

collecting and treating a nucleoprotamine from a developmental stage of a life form by homogenization in an aqueous buffered salt solution at a pH of approximately 2.2 to obtain a mixture;

removing insoluble matter from the mixture of said collecting and treating step;

isolating protein from the mixture by a first aqueous chloroform extraction;

removing lipids from the isolated protein by a second chloroform aqueous extraction;

performing dialysis of the protein obtained by the second extraction, against sterile water, to remove excess salt; and reconstituting the dialyzed protein with 5% weight/volume heterologous or 5% weight/volume homologous DNA; and, sterile filtration to obtain an aqueous protamine-DNA complex.

2. The process according to claim 1, further consisting essentially of the step of separating of discrete protein peaks by chromatography.

3. The process according to claim 1, wherein said developmental stage of said life form is fertilized egg.

4. The process according to claim 1, wherein said removing of insoluble matter from said mixture occurs by ultracentrifugation.

5. The process according to claim 1, further consisting essentially of the step of encapsulating said aqueous protamine-DNA complex in a carrier substance.

6. The process according to claim 1, further consisting essentially of the steps of:

precipitating said aqueous protamine-DNA complex in water; and, lyophilizing to remove said water and to produce a solid form of the protamine-DNA complex.

7. The process according to claim 6, further consisting essentially of the step of encapsulating said solid protamine-DNA complex in a carrier substance.

8. A process for providing a high-purity protamine-DNA complex, consisting essentially of the sequential steps of:

collecting and treating a nucleoprotamine from any developmental stage of a life form by homogenization in a buffered aqueous 4M salt solution at a pH of approximately 2.2 to obtain a mixture;

removing insoluble matter from the mixture of said collecting and treating step;

isolating protein from the mixture by a first aqueous chloroform extraction;

removing lipids from the isolated protein by a second aqueous chloroform extraction;

reconstituting the protein obtained by the second extraction with heterogenous DNA of a target tissue;

performing dialysis of the reconstituted protein, against sterile water, to remove excess salt; and, sterile filtration to obtain an aqueous protamine-DNA complex.

9. The process according to claim 8, further consisting essentially of the step of separating of discrete protein peaks by chromatography.

10. The process according to claim 9, wherein said chromatography is alumina and is developed by an aqueous $K_2HPO_4$ buffer.

11. The process according to claim 8, wherein said developmental stage of said life form is egg.

12. The process according to claim 8, wherein said salt solution is sodium chloride and said buffer is sodium citrate.

13. The process according to claim 8, wherein said removing of insoluble matter from said mixture occurs by ultracentrifugation.

14. The process according to claim 8, further consisting essentially of the step of encapsulating said aqueous protamine-DNA complex in a carrier substance.

15. The process according to claim 8, further consisting essentially of the steps of:

precipitating said aqueous protamine-DNA complex in water; and, lyophilizing to remove said water and to produce a solid form of the protamine-DNA complex.

16. The process according to claim 15, further consisting essentially of the step of encapsulating said solid protamine-DNA complex in a carrier substance.

17. A process for providing a high-purity protamine-DNA complex, consisting essentially of the sequential steps of:

collecting and treating a nucleoprotamine from a developmental stage of a life form by homogenization in an aqueous buffered salt solution to obtain a mixture;

removing insoluble matter from the mixture of said collecting and treating step;

isolating protein and removing lipids from the mixture by a single aqueous chloroform extraction;

performing dialysis of the protein obtained by the second extraction, against sterile water, to remove excess salt; and, reconstituting the dialyzed protein with 5% weight/volume heterologous or homologous DNA;

and, sterile filtration to obtain an aqueous protamine-DNA complex.

18. The process according to claim 17, further consisting essentially of the step of separating of discrete protein peaks by chromatography.

19. The process according to claim 17, wherein said developmental stage of said life form is fertilized egg.

20. The process according to claim 17, wherein said removing of insoluble matter from said mixture occurs by ultracentrifugation.

21. The process according to claim 17, further consisting essentially of the step of encapsulating said aqueous protamine-DNA complex in a carrier substance.

22. The process according to claim 17, further consisting essentially of the steps of:

precipitating said aqueous protamine-DNA complex in water; and, lyophilizing to remove said water and to produce a solid form of the protamine-DNA complex.

23. The process according to claim 22, further consisting essentially of the step of encapsulating said solid protamine-DNA complex in a carrier substance.

24. A process for providing a high-purity protamine-DNA complex, consisting essentially of the sequential steps of:

collecting and treating a nucleoprotamine from any developmental stage of a life form by homogenization in a buffered aqueous salt solution, to obtain a mixture;

removing insoluble matter from the mixture of said collecting and treating step;

isolating protein and removing lipids from the mixture by a single aqueous chloroform extraction;

reconstituting the protein obtained by the second extraction with heterogenous DNA of a target tissue;

performing dialysis of the reconstituted protein, against distilled water, to remove excess salt; and, sterile filtration to obtain an aqueous protamine-DNA complex.

25. The process according to claim 24, further consisting essentially of the step of separating of discrete protein peaks by chromatography.

26. The process according to claim 25, wherein said chromatography is alumina and is developed by an aqueous $K_2HPO_4$ buffer.

27. The process according to claim 24, wherein said developmental stage of said life form is egg.

28. The process according to claim 24, wherein said salt solution is sodium chloride and said buffer is citric acid.

29. The process according to claim 24, wherein said removing of insoluble matter from said mixture occurs by ultracentrifugation.

30. The process according to claim 24, further consisting essentially of the step of encapsulating said aqueous protamine-DNA complex in a carrier substance.

* * * * *